United States Patent [19]
Henry et al.

[11] 3,939,599
[45] Feb. 24, 1976

[54] POLISHING DEVICE

[75] Inventors: Ormond L. Henry, Muskegon; Raymond P. Smith, Southfield, both of Mich.

[73] Assignee: D & H Industries, Inc., Oxen Hill, Md.

[22] Filed: July 12, 1973

[21] Appl. No.: 378,773

[52] U.S. Cl. .................................... 32/59; 15/28
[51] Int. Cl.² ........................................ A61C 3/06
[58] Field of Search .......... 32/58, 59; 15/28, 22, 23; 310/50

[56] References Cited
UNITED STATES PATENTS

| | | | |
|---|---|---|---|
| 3,509,629 | 5/1970 | Kidokoro et al. | 32/27 |
| 3,675,330 | 7/1972 | Drapen | 32/59 |
| 3,757,419 | 9/1973 | Hopkins | 32/59 |

*Primary Examiner*—Robert Peshock
*Attorney, Agent, or Firm*—McGarry & Waters

[57] ABSTRACT

A tooth polishing device wherein a polishing tool is secured to a power drive assembly and the power drive assembly is pivotably mounted in a casing for rotational movement within the casing. A power supply means includes a switch and is coupled to the power drive assembly for supplying electrical power thereto. The switch includes a biasing means, for example, a leaf spring contact, biasing the power drive means to one rotational position within the casing. The switch is open when the power drive is in the one position and is closed when the power drive means is moved rotationally to a second position. The spring contact is mounted on the motor of the power drive assembly and bears against the bottom portion of the casing. The casing is sealed, and is provided with a battery for operating the power supply assembly. Recharging contacts are provided in the casing for recharging the battery when the polishing device is not in use. The battery and power supply are mounted in tandem within the casing which is elongated in shape to facilitate holding and operation of the polishing device. A novel gear reducer is provided in the power drive assembly.

14 Claims, 7 Drawing Figures

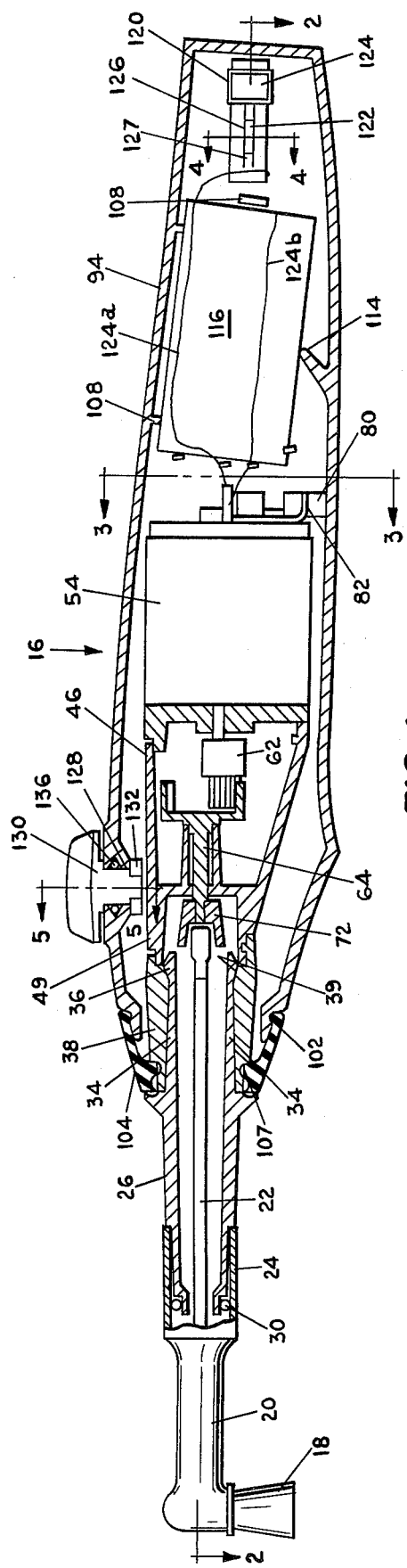

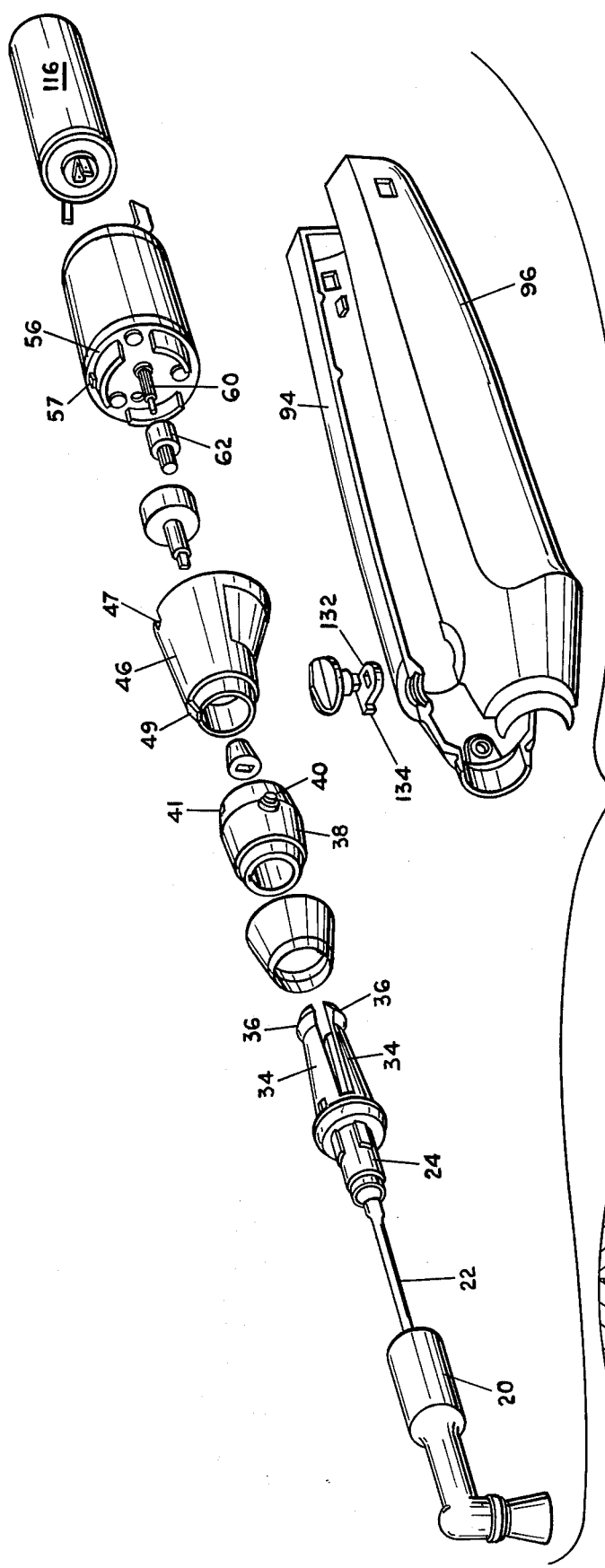
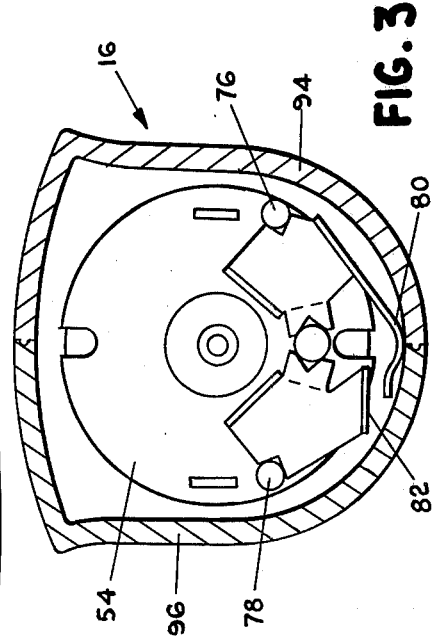
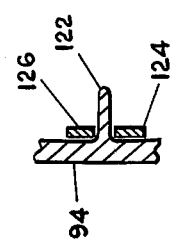
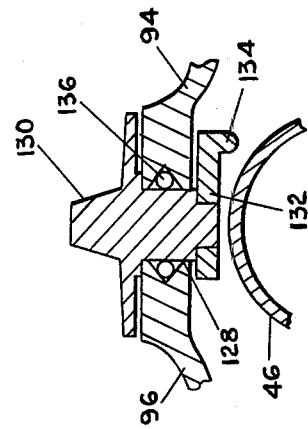
FIG. 6
FIG. 5
FIG. 4
FIG. 3

POLISHING DEVICE

BACKGROUND OF THE INVENTION

1. Field of the Invention

This invention relates to polishing devices of a type used for polishing teeth. In one of its aspects, the invention relates to a polishing device which can be operated by use, i.e., in the normal course of use of the device, or can be operated by a manual switch.

In still another of its aspects, the invention relates to a sealed battery operated polishing device which can be recharged for long life.

2. State of the Prior Art

In U.S. Pat. No. 3,675,330 to Drapen and Henry, there is disclosed and claimed a tooth polishing device wherein a polishing element is rotatably driven by a motor assembly. In one embodiment, the motor is mounted within a casing which is pivotably mounted within a second casing. A switch is provided within the second casing and bears against the first casing so that when the casing is rotated, as by pressure on the polishing element, the switch is closed to supply electrical current to the motor. A spring between the second casing and the first casing biases the first casing into a position at which the switch is open. The polishing element in the second embodiment is provided at right angles to the axis of the motor drive mechanism so that pressure upon the polishing element in the normal course of operation will operate the switch.

Dayton et al. in U.S. Pat. No. 3,106,732 disclose a work actuated rotary brush in which pressure on the brush itself operates the power drive for the brush. In one embodiment, the motor is axially slidable within the casing to operate a switch. In another embodiment, the brush is at right angles to the drive mechanism and the brush is connected to the drive mechanism through a clutch which is engaged by pressure on the brush. In still another embodiment, a pair of batteries is electrically connected in tandem to the motor within the casing.

Dayton et al. in U.S. Pat. No. 3,220,039 discloses still another type of motor driven tooth brush wherein the brush is at right angles to the handle and drive shaft for the brush. The casing is constructed in much the same fashion as a flashlight with a motor and drive shaft in a front portion of the casing and a battery at a rear portion of the casing. An axially slidable switch completes the circuit between the battery and the motor to operate the rotary brush. The ends of the casing are closed by removable caps for assembly and so that the battery and other working parts of the implement can be replaced.

SUMMARY OF THE INVENTION

According to the invention, an improved polishing device employs a sealed casing to prevent water and other materials from seeping into the casing during operation of the device and from corroding the electrical contacts and other electrical components of the device. The polishing device according to the invention is easily assembled from a number of parts which snap-fit together, eliminating expensive assembly operations. The device also provides a simple manual switch to operate the power supply assembly or the assembly can be operated by pressure on the polishing implement. A battery is sealed into the casing in tandem with the motor so that there is an elongated casing to facilitate handling and use of the device. Rechargeable contacts are provided on the casing for recharging the battery without removal from the casing.

In the improved polishing device, a polishing tool is secured to a power drive means and the power drive means is pivotably mounted within a casing for movement between first and second positions within the casing. Power supply means, including a switch, are coupled to the power drive means for supplying electrical power thereto. The switch includes means for biasing the power drive means to the first position wherein said switch is open. Movement of the power drive means to the second position within the casing closes the switch for supply of power to the power drive means.

The polishing tool is desirably of the type which is at right angles to the shaft of the drive means. The polishing tool is indexed with the power drive means so that pressure on the polishing tool will force the power drive assembly from the first position to the second position within the casing as pressure is applied to the tool, thereby closing the switch.

The switch is preferably a leaf spring type and is mounted directly on the power drive assembly so that a portion of the leaf spring bears against the casing. The leaf spring flexes upon rotation of the power drive means and is forced in contact with a fixed contact member on the power drive assembly.

The power drive means is composed of a plurality of parts which are indexed and snap-fit together into a rigid assembly so that the entire assembly moves as a unit. A flexible sealing gasket is provided between the casing and the power drive means so that the casing is completely sealed, yet the power drive means is movable with respect to the casing.

BRIEF DESCRIPTION OF THE DRAWINGS

The invention will now be described with reference to the accompanying drawings in which:

FIG. 1 is a side elevational view in section of a tooth polishing device according to the invention;

FIG. 2 is a sectional view taken along lines 2—2 of FIG. 1;

FIG. 3 is a sectional view taken along lines 3—3 of FIG. 1;

FIG. 4 is a partial sectional view seen along lines 4—4 of FIG. 1;

FIG. 5 is a partial sectional view taken along lines 5—5 of FIG. 1; and

FIG. 6 is an exploded view of the tooth polishing device;

DESCRIPTION OF THE PREFERRED EMBODIMENT

Figure 7:
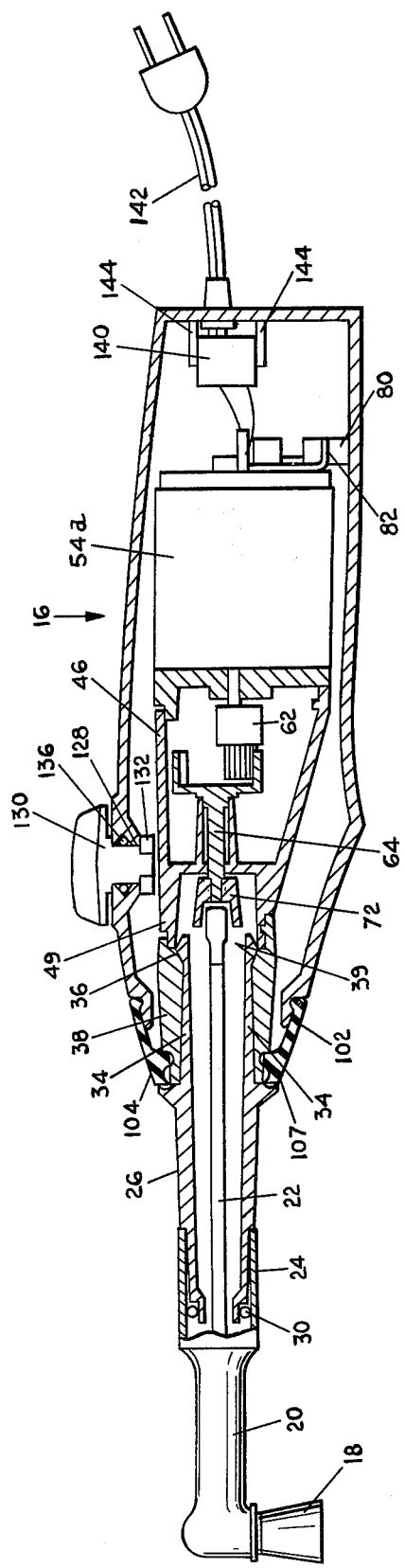
FIG. 7 is a view similar to FIG. 1 of a modified form of the invention.

Referring now to the drawings, and to FIGS. 1, 2 and 6 in particular, there is shown a tooth polishing device having a polishing cup 18 secured to a polishing head 20. A drive rod 22 projects rearwardly from the polishing head 20. Such polishing heads are well known devices which are conventionally used on professional dental equipment found in dentists' offices. Such polishing heads 20 have bevel gears (not shown) at the forward portion which are connected to the drive rod 22 to drive the cup 18 about an axis perpendicular to the axis of the drive rod 22 in conventional fashion. The drive rod 22 is conventionally provided with a lower rectangularly shaped end 23 for engagement with a driving mechanism. As illustrated in FIGS. 1 and 2, the polishing head 20 is provided with an annular bottom portion 24.

The polishing head is mounted on a rigid power drive assembly which includes coupling 26, pivot members 38, bearing housing 46 and motor 54. The power is supplied to the drive rod 22 from the drive shaft 60 of the motor 54, through a drive chain which includes a drive gear 62, drive connection 64 and coupler 72. The entire power drive assembly and drive chain pivot as a unit within the casing 16.

The tubular coupling 26 mounts the annular bottom 24 of the polishing head 20 through a friction fit. To this end, the coupling 26 has a reduced forward section 28 in which an O-ring seal 30 is provided. The O-ring seal 30 seals the joint between the coupling 26 and the polishing head 20.

The coupling 26 has a pair of fingers 34 (seen best in FIG. 6) with enlarged lower ends 36 having outwardly tapering surfaces. The annular pivot member 38 is snap-fit into engagement with the coupling 26 through the fingers 34 as illustrated in FIGS. 1 and 2. The lower end of the pivot member 38 has outer tapering surfaces 39 at the inner diameter thereof, with the tapered surfaces 39 complementing the outwardly tapering surfaces of the enlarged lower end 36. Thus, the coupling 26 is retained on the annular pivot member 38 through the fingers 34.

A pair of pivot pins 40 project laterally outwardly from the pivot member 38 to pivotably support the power unit in the casing in a manner which will be described later. The lower portion of the annular pivot member 38 has a connecting annulus 42 with radially projecting tabs 34. The bearing housing 46 has indentations 48 at an upper portion which engage the tabs 44 so that the bearing housing 46 snap-fits into engagement with the pivot member 38. The bearing housing 46 has a central bearing member 50 provided with an axial opening extending therethrough for the drive chain. At the lower portion, the bearing housing 46 has radial tabs 52 for snap-fit engagement with the motor 54.

A front mounting plate 56 is secured to the motor 54 and is provided with three spaced connected projections 58, each of which has an indentation 59 for engagement with the radial tabs 52 of the bearing housing 46. As seen in FIG. 6, the bearing housing 46 has a centering slot 47 at a rear portion thereof for engagement with a centering projection 57 on the front mounting plate 56 so that precise alignment is maintained between the bearing housing 46 and the mounting plate 56. In a similar manner, the bearing housing 46 is provided with a raised lug 49 at a front portion thereof for engagement with a slot 41 in the pivot member 38. In this manner, the position of the motor 54 with respect to the pivot member 38 is assured during assembly.

The drive shaft 60 extending from a front portion of the motor mounts the stepped drive gear 62 and is provided with teeth which drivingly engage the same. Internal teeth (not shown) on the interior surface of the stepped drive gear 62 can be provided to engage the exterior teeth on the drive shaft 60.

A drive connector 64 has an annular bottom portion 66 with a geared internal surface 68. The drive gear 62 drivingly engages the geared inner surface 68 of the drive connection 64 as seen in FIG. 1. The relatively large surface 68 provides a speed reducer for the drive chain. A square upper end 70 is provided at the forward portion of the drive connector 64. A coupler 72 fits on the square upper end 70 and provides a socket for the lower formed end 23 of the polishing head drive rod 22. Thus, the polishing head 18 is driven by the motor 54 through drive shaft 60, stepped gear 62, drive connection 64, coupler 72 and drive rod 22.

Reference is now made to FIG. 3 for a description of the switch used to operate the motor. The switch comprises a pair of poles 76 and 78 which are electrically connected respectively to a spring contact 80 and a fixed contact 82. In normal position, illustrated in FIG. 1, the spring contact 80 is separated from the fixed contact 82 with the bottom of the spring contact 80 resting on the bottom of the casing 16. The spring contact 80 is made from a resilient, conductive material and provides the spring which biases the drive assembly upwardly as viewed in FIGS. 1 and 3. Thus, when the motor 54 is forced downwardly, the fixed contact 82 is brought down into contact with the spring contact 80, thereby completing the electrical circuit for the motor. Power is thereafter supplied to the motor to rotate the polishing cup 18.

Referring again to FIGS. 1 and 2, the casing 16 can be formed in halves 94 and 96 which are substantially symmetrical about the parting line between the two halves. Sockets 98 and 100 are formed in the forward portions of the casing havles 94 and 96 respectively and mount the pivot pins 40 of the pivot member 38. An external groove 102 is formed in a front part of the casing havles 94 and 96 for retaining a tapered annular rubber gasket 104. To this end, the gasket 104 has a slightly oversized radial protuberance 106 which fits into the external groove 102. The forward portion of the gasket 104 sealingly abuts the peripheral abutment 32 of the coupling 26. Further, an inner sealing rim 107 is provided on the rubber gasket 104 for sealingly engaging the forward portion of the pivot member 38. Thus, a seal is maintained between the forward portions of the casing halves 94 and 96 and the coupling 26 and the pivot member 38. Because of the flexible nature of the rubber gasket 104, the seal is maintained between the casing and the coupling 26 as the coupling 26 rotates with respect to the casing 16.

A battery 116 is mounted behind the motor. To this end, the rear portions of the casing havles 94 and 96 have radial positioning lugs 108, a front positioning lug 110, a bottom positioning lug 114, and a rear positioning lug 112. The battery 116 is connected electrically to the poles 76 and 78 through leads 116a and 116b which extend from terminals 118 and 119 respectively.

At the rear-most portion of the casing havles 94 and 96, lateral openings 120 are provided for recharging contacts 124. Radial positioning lugs 122 extend inwardly from the sides of the casing havles 94 and 96 and retain the recharging contacts 124 in position. To this end, slots 126 having retaining lugs 127 in the recharging contacts 124 are provided. The positioning lugs 122 extend through the slots 126 and the retaining lugs 127 frictionally engage and grip the positioning lugs 122. Leads 124a and 124b extend from respective recharging contacts 124 to terminals 118 and 119 of the battery 116.

Referring now specifically to FIGS. 1 and 5, a manual actuator is shown for manually turning the motor on so that it runs continuously, if desired, with or without pressure on the polishing cup 18. A knob 130 is provided in opening 128 in the forward portion of the casing havles 94 and 96. A knob 130 is provided in opening 128 in the forward portion of the casing havles 94 and 96. An O-ring seal 136 provides a seal between the casing havles 94 and 96 and the knob 130. An actuator 132 having a downward projection 134 is secured to the bottom of the knob 130. As seen in FIG. 5, when the motor is in the position illustrated in FIGS. 1 and 2, the projection 134 will lie to one side of the bearing housing 46. As the knob 130 is rotated about its axis, the downward projection 134 bears against the bearing housing 46 to force the motor 54 downwardly as viewed in FIG. 1, thereby forcing the fixed contact 82 into electrical engagement with the spring contact 80. In this position, the knob 130 will be held by friction so that the power drive assembly is locked in the energized position.

When the parts have been assembled in the manner illustrated, the casing halves are welded together to seal the casing shut. The entire unit is thus sealed against water, dirt, etc. The battery 116 is standard 1.25 volt battery which is of the rechargeable type. The battery is recharged through the recharging contacts 124. Recharging current is applied to the contacts 124 by a battery recharging circuit (not shown). Such recharging circuits are well known.

The motor 54 is a standard DC motor, for example, a 1.5 volt motor. Desirably the motor is of the "stall" type such that the motor will cease operation when a predetermined resistance torque is applied to the output shaft. Thus, if an excessive amount of pressure is applied to the teeth by the polishing cup 18, the motor will stop and polishing will be discontinued.

In operation, the motor 54 is actuated to rotate the polishing cup 18 either by applying upward force on the cup 18 as viewed in FIG. 2, (as would be common in an ordinary polishing operation) or by turning the knob 130 in the manner described above. In either case, the motor 54, being secured to the pivot members 38 through the bearing housing 46 and the front mounting plate 58, will pivot downwardly within the casing 16 about the pivot pins 40 of the pivot member 38. This downward movement will cause the fixed contact 82 to come into electrical engagement with the spring contact 80 to thereby complete the electrical circuit between the battery 116 and the motor 54. Thus, the motor, having electrical power supplied thereto, will drive the drive shaft 60, the stepped drive gear 62, the drive connection 64, the drive rod 22, and the cup 18. After the polishing operation is complete, and pressure is released on the cup 18 (or the knob 130 is returned to its initial position), the motor 54 will be forced upwardly back into the position illustrated in FIG. 1 by the spring contact 80 which bears against the bottom surface of the casing 16. Thus, the electrical connection between the spring contact 80 and fixed contact 82 will be broken, thereby cutting off the supply of current to the motor 54.

In FIG. 7, like numerals have been used to designate like parts. In FIG. 7, the polishing device is substantially the same as shown in FIGS. 1-6 except that the battery of the first embodiment has been replaced by a rectifying diode circuit 140 and a cord 142 for supply of 110 volts AC. The rectifying diode circuit is mounted on holders 144 which are molded into the casing 16. The motor 54a is a 110 volt DC motor.

The polishing device according to the invention provides a compact sealed unit made inexpensively from snap-fit plastic parts which can be easily and quickly assembled. The parts themselves are inexpensively manufactured from plastic materials, such as polyvinylchloride, polyethylene, polypropylene, and the like. For example, except for the motor 54, battery 116 and electrical components, and the polishing head 20, all parts can be made from molded plastic or rubber. In order to add strength to the drive mechanism, the coupler 22 can be made of metal.

The polishing device has a sealed casing yet provides for relative movement between the casing and the drive mechanism so that the drive mechanism can be actuated by appropriate pressure on the polishing cup 18. Further, the polishing device according to the invention provides an alternate mode of operation, namely one in which the polishing head is operated automatically when pressure is applied to the polishing cup 18 and one which can be operated manually so that the device is continuously operated regardless of the pressure on the polishing cup 18.

The invention also provides a novel speed reducer so that the polishing cup does not build up excessive friction. The novel speed reducer is conveniently mounted coaxially with a bearing support which is a part of the power drive assembly.

Reasonable variation and modification are possible within the scope of the foregoing disclosure, the drawings, and appended claims without departing from the spirit of the invention.

The embodiments of the invention in which an exclusive property or privilege is claimed are defined as follows:

1. In a tooth polishing device wherein a polishing tool is secured to a power drive means and said power drive means is pivotably mounted in a casing for movement between first and second positions within said casing; and power supply means, including a switch, are coupled to said power drive means for supplying electrical power thereto; the improvement which comprises:

said switch means includes a leaf spring made of a resilient electrically conductive material, said leaf spring mounted at one end to said power drive means and having a free end bearing against said casing, said leaf spring being positioned on said power drive means to bias said power drive means to said first position, said switch means being open when said power drive means is in said first position and being closed when said power drive means is moved to said second position.

2. A tooth polishing device according to claim 1 wherein said power supply means includes a battery mounted in said casing, and further comprising recharging contacts in said casing and electrically connected to said battery for recharging said battery when a recharging potential is applied to said contacts.

3. A tooth polishing device according to claim 2 wherein said casing is elongated and said battery is mounted in tandem with said power drive means.

4. A tooth polishing device according to claim 1 wherein said casing is sealed and said power drive means extend out from one end of said casing; and further comprising flexible sealing means between said casing and said power drive means to seal the joint between said casing and said power drive means.

5. A tooth polishing device according to claim 4 wherein said flexible sealing means is an annular rubber gasket in sealing relationship at one end with said casing and in sealing relationship at the other end with said 6. A tooth polishing device according to claim 1 wherein said polishing tool is removably secured to said power drive means.

7. A tooth polishing device according to claim 1 and further comprising a manually actuatable means mounted on said casing for moving said power drive means from said first position to said second position, and means for locking said power drive means in said second position.

8. A tooth polishing device according to claim 7 wherein said manually actuatable means includes a knob rotatably mounted in sealed relationship in said casing.

9. A tooth polishing device according to claim 1 wherein said power drive means includes a speed reducer and a bearing housing rotatably supporting said speed reducer.

10. A tooth polishing device according to claim 1 wherein said power drive means includes mounting means for said polishing tool, pivot means pivotably mounted in said casing, bearing means mounting a speed reducer gear, and means for securing said mounting means, pivot means, bearing means, and said motor rigidly together in snap-fit relationship.

11. A tooth polishing device according to claim 10 and further comprising means for indexing each of said pivot means, bearing means and motor with respect to each other so that each has a predetermined relationship to the other.

12. A tooth polishing device according to claim 1 wherein said power drive means is biased solely by said leaf spring to said first position.

13. In a tooth polishing device wherein a polishing tool is secured to a power drive means and said powder drive means is pivotably mounted in a casing for movement between first and second positions within said casing and including a motor; and power supply means, including a switch, are coupled to said power drive means for supplying electrical power thereto; the improvement comprising:

said power drive means including a speed reducer gear and bearing means rotatably mounting said speed reducer gear; said speed reducer gear comprises an annular gear member with gear teeth on the inner surface thereof and an output shaft journalled in said bearing means, said bearing means surrounding said annular gear member and attached to said motor, and said motor having a geared output shaft of substantially smaller diameter than the speed reducer gear, said output shaft engaging the teeth of the speed reducer gear, whereby said motor, gear reducer means and bearing means pivot within said casing as a unit.

14. A tooth polishing device comprising in combination:

a polishing tool;

a power drive means mounting said polishing tool for rotation to effect polishing action;

a sealed elongated casing housing said power drive means with said power drive means extending from one end of said casing;

means pivotably mounting said power drive means within said casing;

means sealing the joint between said power drive means and said casing;

a battery mounted in said sealed casing;

means electrically coupling said battery to said power drive means to apply electrical power thereto for operation of said polishing tool, said coupling means including switch means for opening and closing said electrical coupling means upon pivotable movement of said power drive means within said casing; and recharging contacts on said casing and electrically coupled to said battery;

whereby said battery may be recharged while it is in said sealed casing.

* * * * *